United States Patent
Boese et al.

(10) Patent No.: US 8,986,217 B2
(45) Date of Patent: Mar. 24, 2015

(54) MAPPING CATHETER AS WELL AS MAPPING CATHETER APPARATUS AND ASSOCIATED METHOD

(75) Inventors: Jan Boese, Eckental (DE); Norbert Rahn, Forchheim (DE); Bernhard Sandkamp, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 413 days.

(21) Appl. No.: 12/605,547

(22) Filed: Oct. 26, 2009

(65) Prior Publication Data

US 2010/0049011 A1 Feb. 25, 2010

Related U.S. Application Data

(63) Continuation-in-part of application No. 11/653,201, filed on Jan. 12, 2007, now abandoned.

(30) Foreign Application Priority Data

Jan. 13, 2006 (DE) .......................... 10 2006 001 849

(51) Int. Cl.
| | |
|---|---|
| *A61B 5/01* | (2006.01) |
| *G01K 13/00* | (2006.01) |
| *A61B 5/042* | (2006.01) |
| *A61B 5/06* | (2006.01) |
| *A61B 5/00* | (2006.01) |

(Continued)

(52) U.S. Cl.
CPC . *A61B 5/042* (2013.01); *A61B 5/01* (2013.01); *A61B 5/06* (2013.01); *A61B 5/721* (2013.01); *A61B 18/1492* (2013.01); *A61B 2018/00005* (2013.01); *A61B 2018/00011* (2013.01); *A61B 2018/00041* (2013.01); *A61B 2018/00797* (2013.01); *A61B 2018/00839* (2013.01)
USPC ........................................... 600/549; 374/137

(58) Field of Classification Search
CPC ........ A61B 5/01; A61B 5/015; G01K 13/002; G01K 13/004; G01K 2213/00
USPC .................................. 600/549; 374/100, 137
See application file for complete search history.

(56) References Cited

U.S. PATENT DOCUMENTS

| | | | | |
|---|---|---|---|---|
| 5,529,067 | A * | 6/1996 | Larsen et al. ................. | 600/374 |
| 5,740,808 | A * | 4/1998 | Panescu et al. ............... | 600/424 |
| 6,245,026 | B1 * | 6/2001 | Campbell et al. ............. | 600/549 |

(Continued)

FOREIGN PATENT DOCUMENTS

WO       WO 03/057040 A1       7/2003

OTHER PUBLICATIONS

Mark E. Brezinski, Gary J. Tearney, Stephen A. Boppart, Eric A. Swandon, James F. Southern, and James G. Fujimoto, "Optical Biopsy with Optical Coherence Tomography: Feasibility for Surgical Diagnostics", Journal of Surgical Research, Jul. 15, 1997, pp. 32-40, vol. 71, No. 1, Article No. JR964993.

*Primary Examiner* — Max Hindenburg
*Assistant Examiner* — John Pani

(57) ABSTRACT

The invention relates to a mapping catheter for determination of data of an area of an organ embodied as a flat surface, especially of the heart, to be presented graphically, with at least one thermosensor essentially aligned in the direction of the longitudinal axis of the mapping catheter for determination of temperature-related data which is arranged at a tip of the mapping catheter being provided in the distal area of the mapping catheter for introduction into the organ.

11 Claims, 4 Drawing Sheets

(51) Int. Cl.
*A61B 18/14* (2006.01)
*A61B 18/00* (2006.01)

(56) References Cited

U.S. PATENT DOCUMENTS

| | | | |
|---|---|---|---|
| 6,763,261 | B2 | 7/2004 | Casscells, III et al. |
| 6,837,886 | B2* | 1/2005 | Collins et al. .................. 606/41 |
| 7,004,911 | B1* | 2/2006 | Tu et al. ........................ 600/549 |
| 7,153,273 | B2* | 12/2006 | Korotko et al. ............... 600/549 |
| 2002/0048310 | A1* | 4/2002 | Heuser .......................... 374/141 |
| 2002/0161351 | A1* | 10/2002 | Samson et al. ................ 604/507 |
| 2003/0199768 | A1* | 10/2003 | Cespedes et al. ............. 600/473 |
| 2004/0073132 | A1* | 4/2004 | Maahs et al. .................. 600/549 |
| 2005/0203382 | A1 | 9/2005 | Govari et al. |

* cited by examiner

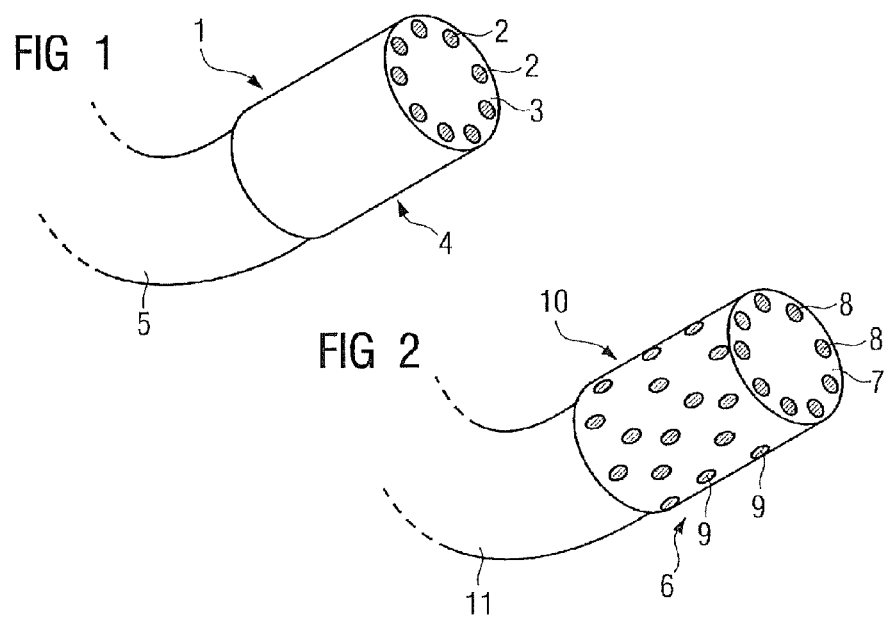
FIG 1
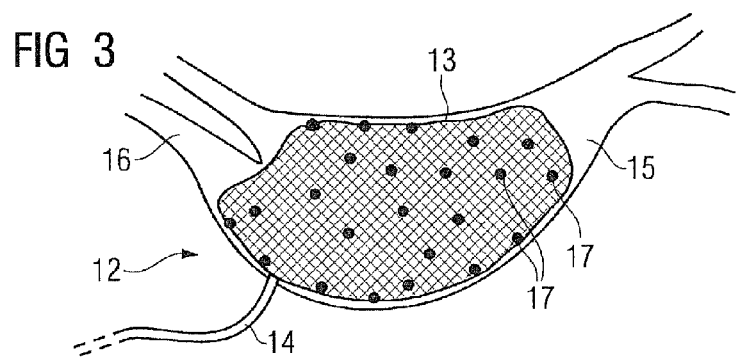
FIG 2
FIG 3
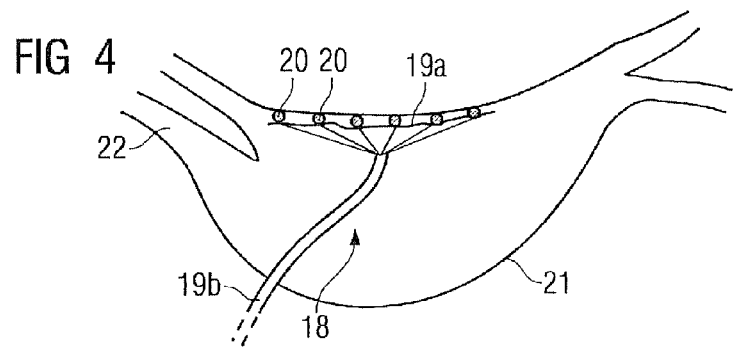
FIG 4

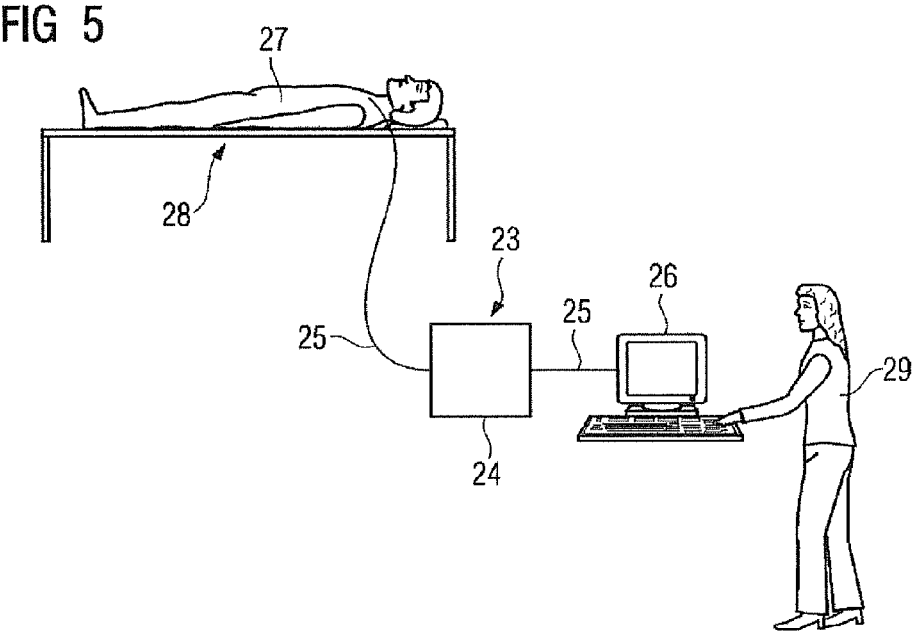
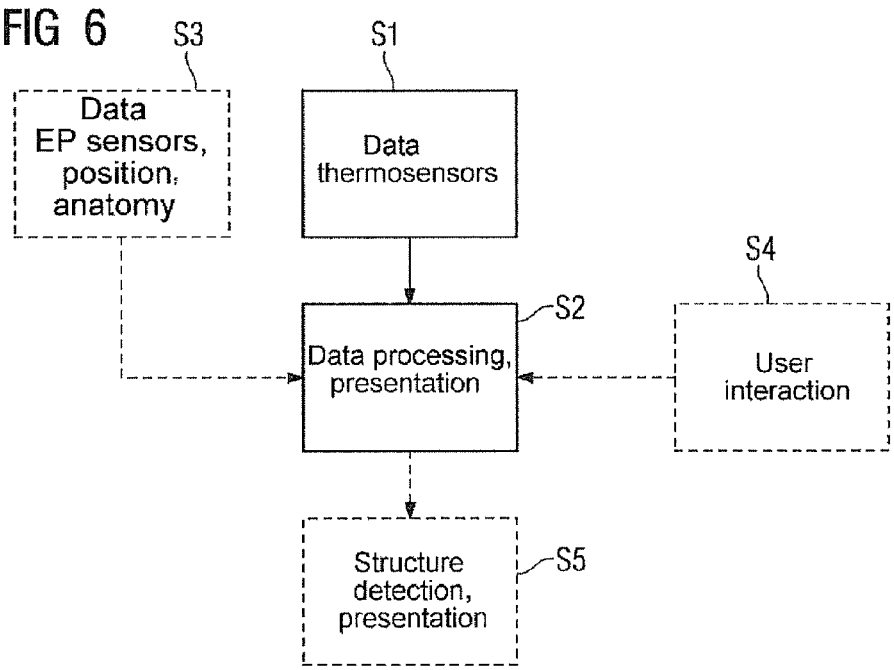

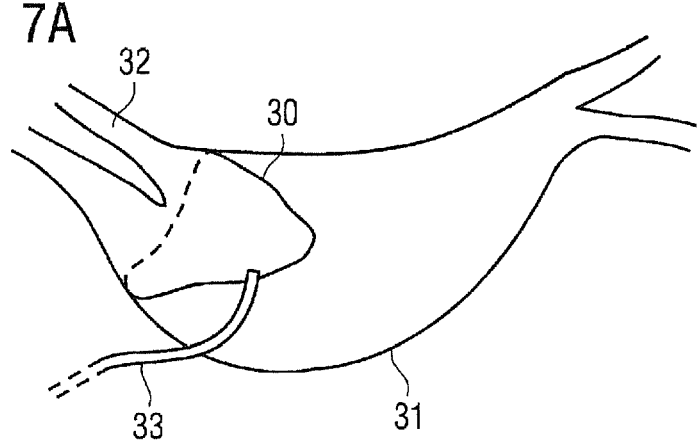
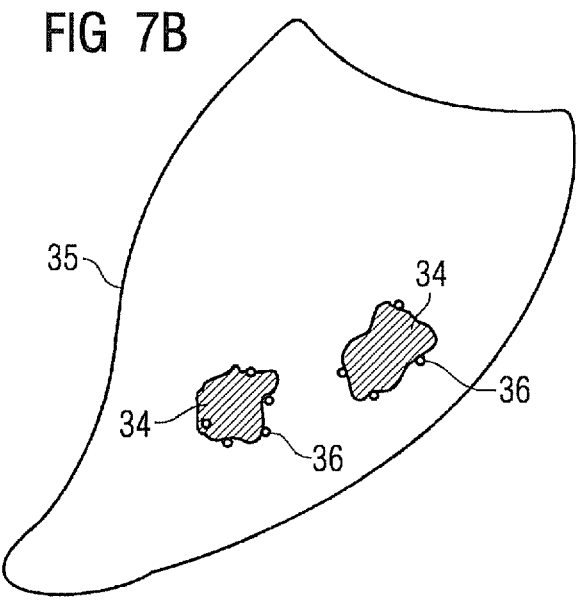

MAPPING CATHETER AS WELL AS MAPPING CATHETER APPARATUS AND ASSOCIATED METHOD

CROSS REFERENCE TO RELATED APPLICATIONS

This application is a continuation-in-part of U.S. Pat. No. 11/653,201 filed on Jan. 12, 2007. This application claims priority of German application No. 10 2006 001 849.4 filed Jan. 13, 2006. All applications are incorporated by reference herein in their entirety.

FIELD OF THE INVENTION

The invention relates to a mapping catheter for determination of data of an area of an organ embodied as a flat surface, especially of the heart, able to be presented as graphical data, as well as to an associated apparatus and an associated method.

BACKGROUND OF THE INVENTION

Mapping catheters are known from electrophysiological applications in which catheters are used to generate images, with which for example voltages or excitations in tissue are recorded, and these values are used for a later visualization. Examples of electrophysiological processes are for example high-frequency ablation procedures, in which lesions are created with the aid of an ablation catheter for example in the endocard or in the epicard of the heart, to remove pathological excitation centers or conduction centers and thereby to treat arrhythmias.

In addition a reduced perfusion of anatomical areas in the heart, but also in other organs, can give rise to cicatricial tissue which in the area of the heart muscle for example can lead to pathological conduction centers which can trigger arrhythmias of the heart chamber, known as atrial fibrillation.

Catheters are also used in other areas of visualization processes, delivering data from which images can be created, with this being done for example under the direction of a technician or a scientist. As a result the images can be used to make decisions relating to diagnoses or treatment techniques.

An x-ray imaging process is currently undertaken to visualize an ablation catheter for example, but this does not result in a sufficiently good visualization in respect to the anatomy of the heart for example. In addition electroanatomical imaging systems are used to represent data relating to the position or orientation of the catheter together with voltage or excitation images. If necessary overlaying techniques are used to represent the morphology together with the electroanatomical data or the catheter.

The images available to date however only provide restricted information, in which anatomical structures and changes of a pathological nature or changes caused by previous treatments and such like can only be seen inadequately or cannot be seen at all.

SUMMARY OF THE INVENTION

The underlying object of the invention is thus to provide a mapping catheter improved in this respect as well as a mapping catheter apparatus and an associated method.

To achieve this object the invention makes provision, with a mapping catheter of the type stated at the beginning, in the distal area of the mapping catheter provided for introduction into the organ, for at least one thermosensor for determining temperature-related data to be arranged at a tip of the mapping catheter essentially aligned in the direction of the longitudinal axis of the mapping catheter.

The catheter thus features, in the direction in which it is guided, meaning the axial direction, a temperature or thermosensor pointing forwards, with which temperature-related data can be determined, which thus senses a change or generates measurement data depending on the ambient temperature or the thermal conditions of the environment of a tissue or material touched by the thermosensor. The thermosensor is essentially aligned in the direction of the longitudinal axis of the catheter, i.e. in an axial direction, with an arrangement in parallel to the longitudinal axis, if necessary at a certain distance from it, also being recorded. The tip of the catheter can if necessary be embodied flat for this purpose, so that if necessary a number of sensors, pointing forwards in each case, are accommodated on it.

The basic idea of using thermosensors is that areas of the organ through which blood flows less strongly, for example endocard or epicard areas with a lower blood flow, have a lower temperature than normal areas with a strong blood flow. A reduced blood flow can be caused for example by changes in the anatomy such as for example lesions after ablations or through cicatricial tissue for example after a myocardial infarction. This means that a better visualization of anatomical or pathological peculiarities, which have a role to play especially in electrophysiological treatments, is possible.

In addition the invention relates to a mapping catheter for determining data able to be presented as images of an area of an organ embodied as a flat surface, the outstanding feature of which is that in the distal area of the mapping catheter, provided for introduction into the organ, at least one element which can be folded out into a gird-like structure is provided, on which at least one thermosensor is arranged for determination of temperature-related data. This mapping catheter thus likewise features one or more thermosensors, which, depending on the ambient temperature or the temperature of tissue touched by the catheter, can sense changes or record and forward data. These thermosensors are accommodated on a grid-like structure which is embodied for example in the form of a net or mesh, if necessary made of a metallic material or of wire.

The grid-like structure expediently has the characteristic of enabling blood to pass through it so that the flow of blood in the area of the organ, which in particular can be a hollow organ, is not adversely affected. The structure involved is thus one which allows material to pass through it, in which sensors are arranged at the points of the grid for example.

Naturally the thermosensors of the grid-like structure can also be aligned in an axial direction pointing forwards. Likewise it is possible for thermosensors to be provided on a grid-type structure in addition to one or more thermosensors at the tip of the mapping catheter, as described above.

In accordance with the invention at least one grid-type structure can be embodied in the unfolded state as an open surface, especially as a screen-type surface, or as a closed surface, especially as a balloon-type surface. Thus for example a wire mesh can be folded out into a screen-type structure, on which thermosensors are arranged over a specific area in order to detect temperature data over a larger surface or at a number of points of the endocard for example. In addition it is possible for the grid or the mesh to be unfolded into a closed form similar to a balloon, in order in this way to achieve contact with the surrounding tissues such as the endocard all the way round.

A number of thermosensors can be arranged in the distal area of the mapping catheter, which, in the unfolded state if necessary, are aligned at least partly in different directions. Examples which can be mentioned are arrangements of around 5 to 100 sensors for example such that a catheter tip which is embodied as a flat surface features up to 10 sensors or a grid-type structure is equipped at various grid points with around 10 sensors which can measure the ambient temperature or the tissue temperature. Alignment in different directions, i.e. not necessarily in the direction of the movement of the catheter, enables the structure of the organ to be understood or covered.

The thermosensors can be aligned at least partly essentially radially and/or diagonally to the longitudinal axis of the mapping catheter. Wall structures, of vessels or tubular organs for example, can be recorded by radially-aligned thermosensors, whereby with an arrangement on grid-type meshes, the inner area of larger hollow organs can also be covered by thermosensors. For this purpose a diagonal alignment of the sensors may be required if the shape of the organ deviates from an essentially cylindrical form, for example for recording the temperatures of the atria or of the ventricles of the heart.

The thermosensor or thermosensors can be aligned to place it or them on the area of the organ embodied as a flat surface. Thus with at least one sensor, as a rule with a plurality of sensors, the temperature can be determined directly on the surface of the organ. If a number of sensors are on the surface of the organ simultaneously, the sensors, where necessary using suitable signal lines, can deliver temperature data of different organ areas at the same times, which can subsequently be compared to each other in order to detect differences. Direct application to the internal area or external area of the organ prevents measurement errors, caused by surrounding blood for example.

In addition the mapping catheter can feature means for, especially local, cooling and/or heating of at least one part of the area of an organ embodied as a flat surface, preferably in the area of at least one thermosensor. With the means for cooling down or heating-up of tissue or of a local area of tissue it is possible to not only measure absolute differences in temperature but to focus on the temperature changes after a cooling down or heating up which expediently is undertaken for this purpose in the area of the thermosensor or thermosensors. Thus, as regards the even temperature environment, it is easier to make possible an exact distinction between the temperatures or the temperature differences.

In accordance with the invention the means can comprise at least one cooling element, especially a Peltier element, and/or at least one heating element, especially a heating coil and/or a lumen for injecting a cold and/or hot liquid, especially a saline solution.

With the mapping catheter which is embodied as a thermocatheter with a temperature sensor, a specific area of the endocard or epicard can be cooled down for example. As a result the temperature increase can be measured after a specific, predeterminable period of time or at intervals. For cooling down a cold liquid, for example a saline solution, can be introduced through the catheter, with the introduction of the liquid expediently being as precise as possible or being undertaken in the area of the position at which the temperature measurement is subsequently to be performed.

Furthermore a Peltier element or further means for local cooling-down or heating up, for example a heating coil, can be provided on the mapping catheter in addition to the one or more temperature sensors or thermosensors, for example at the catheter tip. If necessary the mapping catheter can be equipped with a number of cooling-down or heating-up means which can be replaced if necessary. With these a temperature change can be artificially induced in the vicinity of the thermosensors in different ways depending on the application, after which the temperature curve can be measured with the help of a control device of an associated mapping catheter apparatus in order to obtain a temperature curve over time in this way.

In addition the mapping catheter can feature at least one sensor for determining electrophysiological data and/or a position sensor system. Further sensors can be used for example to record physiological or biometric data. The mapping catheter is expediently equipped with additional sensors which can be used for example used to record voltage or excitation data. This data can then be recorded to supplement the thermodata and used for better visualization by an associated mapping catheter apparatus. If necessary a number of additional sensors and especially a position sensor system can be provided for recording the position and orientation. The position sensor system, typically embodied as an electromagnetic system, can be used to ensure that the position of the catheter in the organ is known at all times and, for a known position of the other sensors, can be related to the recorded data order to make possible a presentation of this data together with anatomical and morphological data with as few errors as possible. Thus different points in the organ area, for example different points of the endocard or epicard, can be sensed one after another and the data determined by means of the mapping catheter can be reconstructed afterwards within the framework of further processing into a three-dimensional map of the sensed area.

Further data such as physiological or biometric parameters can be recorded via one or more sensors and transmitted to a corresponding apparatus. An example which can be given for this process is the determination of metabolism parameters which can provide information about a reduced perfusion of different areas of the heart.

In addition the invention relates to a mapping catheter apparatus with a mapping catheter in accordance with one of the previous claims which stands out in that the mapping catheter apparatus features a control device which is embodied for defining and/or interrogating the temperature-related data of the at least one thermosensor and/or for processing the data, especially for graphical representation of the data on an image output means with the aid of a program means. The data determined by the thermosensor or the number of thermosensors in relation to specific temperatures or thermal conditions is thus at least interrogated or if necessary further defined by the control device by the determined raw data of the sensors being related to temperature values for example. For example thermosensors can be used in which the chemical processes run at specific temperatures or which experience changes of state, for example a color change, whereupon this temperature-related data is fed via a corresponding data connection to the control device of the mapping catheter apparatus, which from this data undertakes a further determination of the temperature-related data in the sense of a conversion into relative or absolute temperature values. Further data processing by the control device can be undertaken by conversion of the data, if necessary by a combination with electrophysiological or anatomical data, for a graphical presentation, to which end a suitable parameter package is available if necessary to perform the computation of the data.

The control device is advantageously embodied for determining and/or interrogating and/or processing the data at least approximately in real time. Optimum support can be provided for the treatment processes or diagnostic processes, especially by processing the data for a presentation, expediently for a presentation of the temperature data together with further data. For example a real time presentation of thermodata can be used for electrophysiological ablation procedures in which the areas of the organ through which blood flows less strongly can appear greatly accentuated in a corresponding calculation of the temperature data for a graphical presentation. The lower perfusion for example of myocardial areas in which an ablation treatment is being executed can be determined and presented by measuring the temperature and creating a thermomap from this, with this being done if necessary together with morphological data or electroanatomical mapping data.

The control device can, if necessary with the aid of a position sensor system of the mapping catheter, be embodied for detection of the position and/or orientation of the mapping catheter. The data related to the position or the orientation of the catheter can be processed in such a case together with the thermodata and if necessary further available data in order to obtain the most realistic possible representation of the organ area in which the catheter is located. Using the thermodata, which can be well assigned because of the known positioning of the catheter, lesions or cicatricial tissue can be well presented.

The mapping catheter apparatus with the mapping catheter can be embodied as an integrated unit with an ablation catheter and/or an electrophysiological mapping catheter. Such an integration, for example with a single surrounding lumen, enables the steps taken during the ablation treatment to be controlled in the optimum manner by processing the thermodata. Likewise, after the introduction of a single catheter, there can be a comprehensive recording of temperature-related and other data.

In addition the mapping catheter apparatus can feature means for cooling down and/or heating up the blood in contact with the area of the organ embodied as a flat surface, especially an infusion pump to be controlled by the control device with a cooling device. Thus for example the entire blood of a heart chamber to be examined or to be treated can be continuously pumped out with an infusion pump, cooled down by a cooling device and subsequently fed back to the heart. This type of procedure offers the advantage that the cooling-down or the temperature change of the blood prevents different areas of tissue which inherently have different temperature characteristics being evenly heated by blood exerting a heating effect and thus rendering more difficult a good differentiation of the temperatures recorded with the thermosensors.

The thermosensor or the thermosensors, where necessary depending on signals of the control unit, can be embodied for repeated determination of the temperature-related data, especially for continuous determination and/or for determination at specific intervals. Thus especially in the event of a local cooling-down or heating-up, or also a cooling-down or heating-up of the blood being undertaken by a Peltier element or such like, the temperature change can be adjusted over the course of time. To this end measurements can be taken at predetermined intervals or also continuously, with the time-resolved data being transferred in each case to the control device and the latter storing this data or further processing it.

The control device can be embodied for creating a temperature-time profile from the repeated measurements. Thus if necessary the thermodata can be adjusted over the course of time and analyzed if necessary for each individual temperature sensor, with this data processing expediently being undertaken in the control device. Tissue characteristics can be recognized from this, for example the presence of cicatricial tissue. The temperature-time profile for the respective measuring point features characteristic curves which are to be assigned to specific samples for different tissue.

The control device can be embodied in accordance with the invention for triggering the determination of the temperature-related data by a thermosensor or thermosensors, especially for triggering dependent on signals of an electrocardiogram. Such triggering can take place with respect to an optimum joint presentation or overlaying with further data, such as anatomical or electrophysiological data for example. The trigger of an electrocardiogram which is transferred for example via the control device by means of signal lines to the sensors, makes it possible to record the temperature-related data for example in the same heart phase which was or is decisive for recording electrophysiological maps or further image data.

The control device can be embodied for determining temperature gradients from the temperature-related data of the least one thermosensor, especially after a cooling-down or heating-up of the at least one part of the area of an organ embodied as a flat surface or the blood in contact with the area of an organ embodied as a flat surface. The control device computes in this case from the temperature data, especially of a number of sensors which was recorded at different times or over the course of time at different places, the temporal or local relative changes, i.e. the gradients, in order to make possible an improved differentiation in this way. Thus small changes in the temperature which indicate changes in the blood flow through the tissue for which the data was recorded can already be correctly assigned or detected.

Furthermore the invention relates to a method for graphical presentation of temperature-related data of an area of an organ embodied as a flat surface, especially of data determined using a mapping catheter apparatus of the type described, whereby the data on a control device side is presented graphically by means of a program means, especially with the aid of a color and/or brightness encoding in relation for example to at least one anatomical presentation of the organ and/or of the area of the organ on at least one imaging output means. With the inventive method, which can be executed with the support of a technician or scientist or fully automatically, a thermomap is created which shows the area of the organ recorded by a mapping catheter. To this end the temperature data is presented graphically by being integrated into an anatomical presentation. In such cases presentations of structures in the widest sense are regarded as anatomical presentations without any concerns about accuracy. To this end figures can be inserted into the anatomical presentation if necessary, in which case however a specific encoding, for example a color encoding is expediently used.

Furthermore the data can be presented interactively, especially such that a user influences the presentation using operating tools of the program means by using at least one input device. A keyboard, a mouse or an active display or suchlike can be available to the user as input devices, whereby he can have the opportunity to change between an anatomical representation and the representation of the thermodata or to modify an integrated presentation, for example by rotating the presentation or changing the angle of view or suchlike. Accordingly a presentation on a number of screens or a selection of presentation types such as of split-screen presentations for example can be obtained with input devices.

The temperature-related data can be overlaid at least partly with electrophysiological data and/or further data, for example electrophysiological and/or biometric data, and/or presented in free areas of an anatomical presentation to supplement the electrophysiological data and/or further data. For example a superimposition with electrophysiological voltage or excitation timing maps can be undertaken or the temperature-related measured values can, if necessary after a corresponding conversion by the control device, be presented in a free area of an existing map. For example it is conceivable for electrophysiological data to be presented on a specific side of a map surface, whereas on the other side, that is for example on an internal area of an organ which is accessible after a rotation of the presentation of the external area, the thermodata is displayed.

In the presentation of the temperature-related data structures can be detected by means of at least one programming means for image processing and/or pattern detection. It is possible, using such an image processing or pattern detection system, to extract from the temperature map the contours of cicatricial tissue or lesions which have been caused for example by ablation processes. These contours or patterns can be presented overlaid after a further processing or after the evaluation of anatomical image data or electrophysiological maps. In this case it is possible to refer back to specific forms of visualization such as the "endoscopic view" or "fly" process visualization.

Triggered determined temperature-related data can be used for the presentation, especially data determined by means of an electrocardiogram trigger, especially in relation to the anatomical presentation and/or if necessary available electrophysiological data. This makes possible an optimum overlaying or joint presentation of different data in that triggering removes movement artifacts or it is ensured that the data can be assigned to comparable states or phrases, for example the same heart phases.

Recording the temperature makes a better visualization of organ areas possible. In this case the recorded temperature data which was fed to a control device via a signal line from a catheter or out of the memory is processed in the manner described and used for presentation with various other data in order to obtain additional information in relation to specific tissue structures in this way. This is done as described with the aid of a control device to which the data is fed automatically if necessary without further intervention by a user, whereby however the possibility of interaction is expediently provided. This allows a medical technical assistant or other technician to post-edit the representation, where necessary for further evaluation by a doctor, or to produce a presentation in the desired manner in advance of an evaluation. A presentation to accompany examination or treatment, if necessary in real time, is also possible.

BRIEF DESCRIPTION OF THE DRAWINGS

Further advantages, features and details of the invention emerge with reference to the following exemplary embodiments and also from the drawings. The Figures show:

FIG. 1 an inventive mapping catheter with axially aligned thermosensors,

DETAILED DESCRIPTION OF THE INVENTION

Figure 1B:
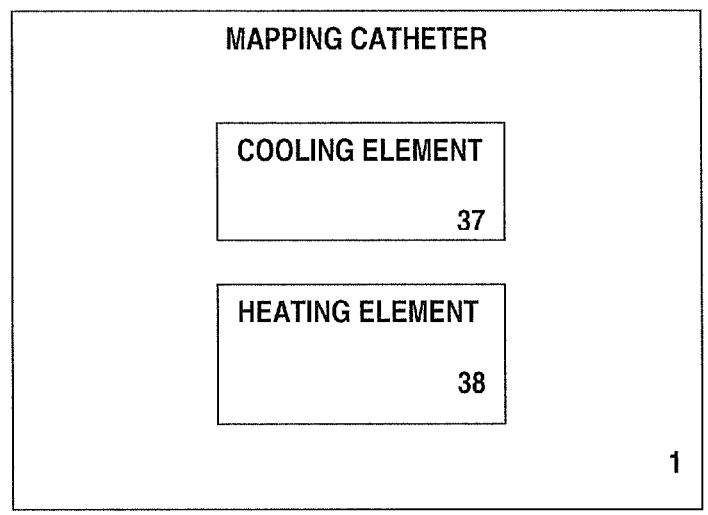
FIG. 1B an inventive mapping catheter showing optional cooling and heating elements in block diagram form without regard to size, shape, and location, FIG. 2 an inventive mapping catheter with axially and radially aligned thermosensors, FIG. 3 an inventive mapping catheter with a balloon-type unfolded grid-like structure with thermosensors, FIG. 4 a inventive mapping catheter with a screen-type unfolded grid-like structure with thermosensors, FIG. 5 the use of an inventive mapping catheter device, FIG. 6 a flowchart of an inventive method, FIG. 7A a diagram for visualization of ablation lesions, and FIG. 7B a diagram for visualization of myocardial cicatricial tissue.

FIG. 1 shows an inventive mapping catheter 1 with axially-aligned thermosensors 2. The thermosensors 2 are arranged on the tip 3 of the distal end 4 of the mapping catheter 1 which is embodied as a flat surface for this purpose. The thermosensors 2 thus point in the direction of the longitudinal axis of the mapping catheter 1 and thereby in the direction of movement of the catheter. Only the front part of the mapping catheter 1 can be seen in the drawing, the remaining area not shown here is merely indicated by a piece of the catheter tube 5 in the drawing. The mapping catheter 1 also has further sensors and means for handling an ablation, which are not shown here. The supply lines are also omitted from the diagram for reasons of clarity, including for example the supply leads to the thermosensors 2 for transmitting the temperature-related data determined to a control device for further processing or for storage. The mapping catheter 1 further comprises a cooling element 37 at the catheter tip 3, especially a Peltier element, and/or a heating element 38 at the catheter tip 3, especially a heating coil.

The tissue of an area of the organ can be sensed with the thermosensors 2 which are arranged on the front of the mapping catheter 1 in order to obtain temperature values in this way. From the temperature values determined with the thermosensors 2 conclusions can be drawn about the flow of blood through the tissue which indicates changes caused by treatments or diseases.

FIG. 2 shows a further mapping catheter 6, also in a sectional view. The mapping catheter 6 features a series of forwards-pointing temperature sensors 8 at its tip 7 which are supplemented by temperature sensors 9 extending in the radial direction in the remaining distal area 10 of the mapping catheter. The catheter tube 11, which is embodied with further components such as drive devices or supply lines, again adjoins the distal area 10 of the mapping catheter 6. The distributed arrangement of the temperature sensors 8, 9 in the distal area 10 or at the tip 7 avoids problems in establishing contact with the area of the organ, for example the heart wall. The mapping-catheter 6 can thus be positioned more easily precisely in complex organ structures, since temperature sensors 8, 9 are always present which have at least approximately the correct orientation for determining a temperature.

FIG. 3 shows an inventive mapping catheter 12 with a balloon-type unfolded grid-like structure 13. The grid-like structure 13 in the distal area of the mapping catheter 12, which was positioned in the atrium of the heart 15 with the aid of the catheter tube, features a series of thermosensors and further sensors which are identified by the common reference symbol 17. The further sensors are (electro)physiological sensors which record data such as voltage data. The vessels 16 are the pulmonary veins which lead to the left atrium of the heart. The heart chambers and the right atrium are not shown. The thermosensors and further sensors 17 are aligned by the unfolding of the grid-like structure 13 in different directions axially, radially and diagonally to the longitudinal axis of the catheter such that they are present in the internal area of the left-hand atrium of the heart 15. The grid-like structure 13 is embodied in this case to allow the passage of blood through it in order not to hinder the circulation of blood during measurement.

A repeated determination of the temperature-related data is possible with the aid of the thermosensors and further sensors 17 which are in contact with the endocard, in order, after a local cooling-down or heating-up of the mapping catheter 12 by means not shown here, to record temperature data over the course of time. This enables peculiarities in the endocard tissue of the atrium of the heart 15 to be better detected.

FIG. 4 shows an inventive mapping catheter 18 with a screen-type unfolded grid-like structure 19a on which a number of thermosensors 20 are arranged. The grid-like structure 19a is embodied as a wire mesh and lies here on a surface of the left-hand atrium 21 in which the oxygenated blood from the lung circulation reaches the heart via the lung veins. The grid-like structure 19a is pushed forwards and unfolded from the catheter tube 19b on reaching the position intended for the measurement. A comparatively large surface can be mapped with the screen-type structure.

The data of the thermosensors 20 is fed via supply leads to a control device of a mapping catheter apparatus which processes it into image data.

FIG. 5 outlines the use of an inventive mapping catheter apparatus 23. The mapping catheter apparatus 23 has a control device 24 which is connected on one side via a data connection 25 to an image output and input device 26, on the other side to a mapping catheter 28 introduced into the body of the patient 27, not shown in greater detail here. The mapping catheter 28 features in its distal area thermosensors with which temperature data of a flat area of an organ is determined. The mapping catheter 28 also has a cooling element for application of a local temperature reduction. The temperature data is subsequently fed to the control device 24 via the data connection 25 which processes this data in order to create a graphical presentation from it on the output and input display device 26. This graphical presentation is available to a user 29 who can interactively influence the presentation, if necessary by making specifications before the measurement is performed which control the sequence of data recording.

The mapping catheter 28 furthermore features sensors, with the aid of which it is possible to position and adjust the position of the mapping catheter to take account of the orientation. In addition the further sensors enable electrophysiological data to be recorded which in its turn again flows into the control device 24 for further processing. In the control device 24 the position data is used for a three-dimensional reconstruction with the presentation of a three-dimensional thermomap for the user 29 at the graphical input and output display 26. If necessary the control device 24 forms gradients of the transferred data and controls the repeated data recording by thermosensors of the mapping catheter 28 such that the different sensor data can be displayed on the graphical output and input device 26 overlaid in the optimum manner.

FIG. 6 shows a flowchart of an inventive method for graphical presentation of temperature-related data of an area of an organ embodied as a flat surface. In this case initially before beginning of the presentation, data is determined in a step S1 with thermosensors which are arranged at least partly in the direction of movement of a mapping catheter at the tip of said catheter or on a grid-like structure of the catheter. This thermodata from step S1 is processed in step S2 with the aid of a control device and converted into a representation of the temperature, to which end facultatively, as indicated here by the dashed lines, data of electrophysiological sensors, that is of EP sensors, as well as on the position of the catheter and the anatomy which will be determined in step S3 is included as supplementary data. The data is transferred automatically to the control device or after polling the sensors.

Furthermore the data processing and presentation is influenced in accordance with step S2 by user actions which can also be undertaken facultatively after step S4. The user in this case can specify how the data is presented via an input device, such as in respect of overlaid presentation or the selection of a specific encoding for the presentation for example, and where necessary can modify the presentation subsequently by rotation using an input tool and such like.

With the aid of the temperature-related data obtained in step S1 a presentation is obtained which delivers important information in respect of the temperature conditions in the organ which in particular allows feedback about the perfusion of the areas involved. Thus areas with lower blood flow such as cicatricial tissue are cooler, thereby exhibiting a lower temperature than areas with normal blood flow. The measurement can be undertaken to an accuracy of around one tenth of a degree and possibly better, so that, by adjusting temperature gradients in the range of one degree, important information from the thermomap which was created in step S2 In accordance with the inventive method can be derived.

In a similarly facultative manner, in step S5, with the aid of a program means available on the control device side, structures can be detected and inserted into the presentation which follow on from the temperature data. Thus lesions or cicatricial tissue can be presented directly, so that a user does not have to only derive such information from the temperature distribution. To this end the control device has corresponding means available for post-processing the presentation after the structure detection. If additional data is available, the data is presented in an overlay map together with electrophysiological and especially anatomical data. If no current anatomical data is fed to the control device, this device access older data of this patient already available in step S2 or data from databases.

The drawing for visualization of ablation lesions in FIG. 7A shows the presentation of a lesion 30 in an anatomical presentation of the left atrium 31 with the pulmonary vein 32 coming out into this chamber. In addition the position and orientation of the mapping catheter 33, which is embodied as an integrated catheter with an additional ablation function, can be seen. The visualization of the ablation lesion 30 enables the ablation treatment to be followed in real time in the optimum manner. Naturally temperature-related images can be created independently of any treatment currently provided with for example thermosensors being provided permanently in the body of the patient, which allows feedback about tissue changes and suchlike.

Finally FIG. 7B shows the visualization of myocardial cicatricial tissue 34 which is likewise presented to a user together with the anatomical structure of the left ventricle 35 on a screen. Pathological excitation centers 36 are present in the area of the myocardial cicatricial tissue 34 which can lead to arrhythmias of the heart chambers. By overlaying electrophysiological data relating to the excitation centers 36 with anatomical data which shows the ventricle 35, with this data being supplemented by the thermodata, which makes precise structuring of the myocardial cicatricial tissue 34 possible, with the aid of an inventive mapping catheter apparatus the extent of the changes present can be detected in the optimum manner and a possible treatment with an ablation catheter can be explicitly undertaken.

The invention claimed is:

1. A mapping catheter apparatus for acquiring data along an area of an organ of a patient, comprising:
   a catheter tube comprising a distal area having a tip configured for introduction into and positioning along the organ;
   a thermosensor array formed in a grid structure adapted to be folded within the catheter tube during introduction and positioning along the organ and adapted to be unfolded outward and pushed forward of the tip to achieve contact with tissues of the organ on reaching a position along the organ intended for measurement, wherein the grid structure allows the passage of blood therethrough when positioned along the organ and comprises a net or a mesh that unfolds into a three-dimensional structure to contact a surface of the organ;

wherein thermosensors in the array are distributed along a plurality of points of the grid structure across the surface area and not solely along a circumference thereof, including distributed in a direction pointing forward of the tip of the catheter tube when the grid structure is unfolded therefrom, to achieve contact with tissues simultaneously at a number of points in the area of the organ, wherein the thermosensors are arranged on the grid structure at a plurality of different radial distances from a given point along a longitudinal axis extending through the catheter tube and extending forward of the tip upon unfolding of the grid structure, wherein the thermosensors further provide temperature related, image forming data corresponding to a thermal gradient detected simultaneously across the area of the organ of the patient where the grid structure achieves contact with tissues;

a control device, coupled to receive the image forming data from the thermosensors of the mapping catheter, configured to generate an image therefrom for display of a graphical presentation of thermal information over the area of the organ; and an image output device coupled to the control device via a data connection to display the graphical presentation as a multi-dimensional thermomap as a function of position data along the area of the organ.

2. The mapping catheter apparatus as claimed in claim 1, further comprising one or more devices in an area of at least one thermosensor for cooling down or heating up a part of the area of the organ.

3. The mapping catheter apparatus as claimed in claim 1, further comprising a sensor for determining data selected from the group consisting of:

electrophysiological data of the patient, physiological data of the patient, biometric data of the patient, and position data of the mapping catheter.

4. The mapping catheter apparatus as claimed in claim 1, wherein the control device processes the temperature related data in real time.

5. The mapping catheter apparatus as claimed in claim 1, wherein the control device detects a position or an orientation of the mapping catheter based on a position sensor system of the mapping catheter.

6. The mapping catheter apparatus as claimed in claim 1, wherein the mapping catheter is integrated with an ablation catheter or an electrophysiological catheter.

7. The mapping catheter apparatus as claimed in claim 1, further comprising a cooling or heating device in an area of at least one thermosensor for cooling down or heating up blood in contact with the area of the organ, wherein the blood is pumped in and out of the area of the organ by the cooling or heating device with an infusion pump controlled by the control device.

8. The mapping catheter apparatus as claimed in claim 7,
wherein the thermosensor repeatedly determines the temperature related data based on a signal of the control device for a continuous determination or a determination at a specific interval, and
wherein the control device determines a profile for temperature vs. time along the area of the organ from the repeated temperature related data.

9. The mapping catheter apparatus as claimed in claim 1,
wherein the control device activates the thermosensor to determine the temperature related data, and
wherein the activation is based on a signal of an electrocardiogram of the patient.

10. The mapping catheter apparatus as claimed in claim 1,
wherein the control device determines a temperature gradient from the temperature related data, and
wherein the temperature gradient is determined after a cooling down or a heating up of at least a part of the area of the organ or blood in contact with the area of the organ.

11. The mapping catheter apparatus of claim 1, wherein the grid structure comprises an irregularly-shaped perimeter, and wherein the thermosensor array comprises a plurality of thermosensors distributed about the irregularly-shaped perimeter.

* * * * *